United States Patent [19]

Horodysky

[11] Patent Number: 4,536,311

[45] Date of Patent: Aug. 20, 1985

[54] MULTIPURPOSE ANTIRUST AND FRICTION REDUCING ADDITIVES AND COMPOSITIONS THEREOF

[75] Inventor: Andrew G. Horodysky, Cherry Hill, N.J.

[73] Assignee: Mobil Oil Corporation, New York, N.Y.

[21] Appl. No.: 566,086

[22] Filed: Dec. 27, 1983

[51] Int. Cl.³ .......................... C10M 1/32; C10M 1/36
[52] U.S. Cl. ................................ 252/51.5 A; 548/347; 548/352
[58] Field of Search .................. 252/51.5 A; 548/347, 548/352

[56] References Cited

U.S. PATENT DOCUMENTS

| Re. 23,227 | 5/1950 | Blair et al. | 548/347 |
|---|---|---|---|
| 3,116,252 | 12/1963 | Beretvas | 252/51.5 A |
| 3,314,968 | 4/1967 | Wakeman et al. | 260/309.6 |
| 3,452,042 | 6/1969 | Mannheimer | 548/354 |
| 4,375,417 | 3/1983 | Zoleski et al. | 252/33.4 |

FOREIGN PATENT DOCUMENTS 1150042  7/1983  Canada .

*Primary Examiner*—William R. Dixon, Jr.
*Assistant Examiner*—C. Johnson
*Attorney, Agent, or Firm*—Alexander J. McKillop; Michael G. Gilman; Howard M. Flournoy

[57] ABSTRACT

Hydroxylalkyl hydrocarbyl imidazoline-acyl sarcosine reaction products exhibit good friction reducing and antirust properties when formulated into a variety of lubricants and fuels at low concentrations.

18 Claims, No Drawings

MULTIPURPOSE ANTIRUST AND FRICTION REDUCING ADDITIVES AND COMPOSITIONS THEREOF

BACKGROUND OF THE INVENTION

This invention is based on the discovery that hydrocarbyl hydroxyalky imidazoline-acyl sarcosine reaction products provide significant friction reducing and antirust properties to a variety of lubricants and fuels when incorporated therein at low concentration. More specifically this invention is directed to hydrocarbyl hydroxyalkyl imidazoline-acyl sarcosine reaction products as multipurpose antirust and friction reducing additives and compositions thereof for lubricants and fuels.

Various amines, amides, oxazolines and imidazolines have been used in the past in commercial lubricant and fuel applications.

U.S. Pat. No. 3,116,252 discloses a rust inhibitor composition comprising a mixture of an acyl sarcosine and a 1,2-disubstituted imidazoline an alkylene oxide-rosin amine reaction product.

U.S. Pat. No. 4,375,417 discloses a cylinder lubricating oil comprising a mineral lubricating oil and overbased calcium sulfonate and a friction modifying amount of at least 1-oxazoline.

The hydroxyalkyl imidazoline-acyl sarcosine reaction products disclosed herein provide advantages in antirust and friction reducing characteristics unavailable in any of the prior art disclosed or known to applicant. Accordingly, the additive compositions as well as the lubricant and fuel compositions made therefrom are believed to be novel and unique the compositions described herein are not believed to have been previously used as multifunctional antirust or friction reducing additives in fluid or solid lubricants or in fuel applications.

SUMMARY OF THE INVENTION

The present invention is directed to hydrocarbyl hydroxyalkyl imadazoline-acyl sarcosine reaction products and to fuel and lubricant compositions containing same. These reaction products when used in additive concentrations of up to about 5% wt. in fully formulated automotive engine oils impart friction reducing characteristics as demonstrated in the Low Velocity Friction Apparatus (LVFA) test as well as protection against copper corrosivity as demonstrated by the well known ASTM D-130-80 Test. This invention is further directed to a method of reducing friction in internal combustion engines and improving inhibition to corrosion of such engines.

Accordingly, the present invention minimizes friction losses and thereby decreases fuel consumption of equipment employing these additive compounds or mixtures thereof as components of lubricating oils or fuels or in fuel mixtures. The products of the present invention are also relatively non-corrosive to copper and can serve to improve the copper corrosivity of normally corrosive lubricants and/or fuels.

DESCRIPTION OF PREFERRED EMBODIMENTS

Typical acyl-sarcosines useful in the present invention include, but are not limited to cocoyl sarcosine, lauroyl sarcosine, oleoyl sarcosine, soya sarcosine, tallowyl sarcosine and related acylated amino acids. Long chain acyl sarcosines are preferred. That is, $C_8$ and above.

Typical hydrocarbyl hydroxyhydrocarbylene imidazolines, which are useful herein, include, but are not limited to products made by the reaction of the appropriate hydroxyl-containing amine with the following acids: oleic acid, stearic acid, isostearic acid, linoleic acid, tall oil acid, lauric acid, myristic acid, coco acids, naphthenic acids, related hydrocarbyl acids and mixtures of these and related hydrocarbyl acids.

The compositions of this invention are usually formed by heating under ambient conditions the imidazoline and acyl sarcosine reactants, preferably in the presence of a suitable hydrocarbon solvent until water evolution stops. Any suitable hydrocarbon solvent known to the art may be used. This reaction may be generalized as follows:

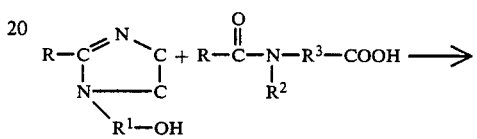

Imidazoline acyl sarcosine reaction products where R is $C_8-C_{30}$ hydrocarbyl, including alkyl, alkenyl, straight chain or branched or cyclic or alkaryl or aralkyl, $R^1$ is $C_2-C_4$ hydrocarbylene, preferably ethylene, $R^2$ is $C_1-C_6$ hydrocarbyl or hydrogen and $R^3$ is $C_1-C_6$ hydrocarbylene, preferably $C_1-C_2$.

Accordingly, the products of the present invention are produced by the reaction of an imidazoline and a sarcosine in a suitable solvent such as, for example, toluene, xylene, or related solvents at temperatures ranging from about 90° C. to about 250° C. Any suitable specific reaction conditions and mole equivalents of the reactants known in the art may be used e.g., in a molar ratio of imidazoline to sarcosine of from about 1:1 to about 1:3. Atmospheric pressure is generally preferred, but higher pressures may be used if so desired.

The additives in accordance herewith may be used effectively to impart to organic media, particularly to greases and lubricating oil and fuels, the properties mentioned hereinabove. An effective amount of the additive compound will range from about 0.1% to about 5% by weight. Preferably, the organic medium or substrate, e.g., oil of lubricating viscosity or grease therefrom, contains from about 0.1% to 5.0% of the additive and more preferably from about 1.0% to about 3.0% by weight thereof, based on the total weight of the lubricant composition. In hydrocarbon fuels, 0.00001% to 0.1% can be used to impart beneficial properties and preferably 0.0001 to 0.00001%. Alcoholic fuels and mixtures of hydrocarbon and alcoholic fuels can also successfully use the present additives.

Of particular significance, in accordance with the present invention, is the ability to improve the resistance to oxidation and corrision of oleaginous materials such as lubricating media which may comprise liquid oils, in the form of either a mineral oil or a synthetic oil, or mixtures thereof, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SUS at 100°

F. to about 600 SUS at 100° F., and preferably, from about 40 SUS to about 250 SUS at 210° F. These oils may have viscosity indexes ranging to about 100 or higher. Viscosity indexes from about 70 to about 95 are preferred. The average molecular weights of these oils may range from about 250 to 800.

Where the lubricant is to be employed in the form of a grease, the lubricating oil is generally employed in an amount sufficient to balance the total grease composition, after accounting for the desired quantity of thickening agent and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment, however, in all other aspects, any materials which are normally employed for thickening or gelling hydrocarbon fluids for forming grease can be used in preparing the aforementioned improved grease in accordance with the present invention. This invention can be used in addition to antiwear, extreme pressure, dispersant, detergent, pour depressant, antifoam and viscosity improving additives and the like in fully formulated lubricant formulations, along with additives such as sulfonates, phenates, succinimides, phosphorodithioates and the like without detracting from the invention.

In instances where synthetic oils, or synthetic oils employed as the vehicle for the grease, are desired in preference to mineral oils, or in combination therewith, various compounds of this type may be successfully utilized. These synthetic oils may be used alone, in combination with mineral oils, or with each other as lubricating oil. Typical synthetic vehicles include synthetic hydrocarbons such as polyisobutylene, polybutenes, hydrogenated polydecenes, the polyglycols, including polypropylene glucol, polyethylene glycol, synthetic ester oils illustrated by trimethylolpropane esters, neopentyl alcohol and pentaerythritol esters, di(2-ethylhexyl)sebacate, di(2-ethylhexyl)adipate, dibutyl phthalate and other types, as for example, flourocarbons, esters of phosphorus-containing acids, liquidureas, ferrocene derivatives, hydrogenated synthetic oils, chain-type polyphenols, siloxanes and silicones (polysiloxanes), alkyl-substituted diphenyl esters typified by a butyl substituted bis(p-phenoxyphenyl)ether.

Having described the invention broadly, the following are offered as specific illustrations. They are illustrative only and are not intended to limit the invention.

EXAMPLE 1

2-Heptadecenyl-1-(2-Hydroxyethyl)Imidazoline/Oleoyl Sarcosine Reaction Product

Approximately 180 g of oleoyl sarcosine (obtained commercially as Hamposyl 0) and 180 g of 2-heptadecenyl-1-(2-hydroxyethyl)imidazoline and 100 g toluene were charged to a one liter reactor equipped with heater, agitator, Dean-Stark tube with condenser and provision for blanketing vapor space with nitrogen. The mixture was heated up to 170° C. over a period of 6½ hours until water evolution during azeotropic distillation ceased. the mixture was vacuum topped to remove volatile materials.

EXAMPLE 2

2-Heptadecenyl-1-(2-Hydroxyethyl)Imidazoline/Cocoyl Sarcosine Reaction Product

Approximately 145 g of cocoyl sarcosine (obtained commercially as Hamposyl C) and 180 g 2-heptadecenyl-1-(2-hydroxyethyl)imidazoline and 100 g toluene were charged to a reactor equipped as described in Example 1. The mixture was heated up to 170° C. over a period of 7 hours until water evolution during azeotropic distillation ceased. The mixture was vacuum topped at 170° C. to remove volatile materials.

Examples 1 and 2 described above were blended into fully formulated mineral and synthetic automotive engine oils containing detergent/dispersant and inhibitor package and evaluated using the Low Velocity Friction Apparatus as shown in Tables 1 and 2.

LOW VELOCITY FRICTION APPARATUS (LVFA)

The Low Velocity Friction Apparatus (LVFA) is used to measure the coefficient of friction of test lubricants under various loads, temperatures, and sliding speeds. The LVFA consists of a flat SAE 1020 steel surface (diameter 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X–Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cammotor arrangement.

Procedure

The rubbing surfaces and 12–13 ml of test lubricants are placed on the LVFA. A 240 psi load is applied and the sliding speed is maintained at 40 fpm at ambient temperature for a few minutes. A plot for coefficients of friction $(U_k)$ vs. speed was taken at 240, 300, 400, and 500 psi. Freshly polished steel specimens are used for each run. The surface of the steel is parallel ground to 4 to 8 microinches. The results in Table 1 refer to percent reduction in friction compared to the unmodified oil. That is, the formulation mentioned above was tested without an added compound of this invention and this became the basis for comparison. The results were obtained at 250° F. and 500 psi, and 40 fpm sliding speed. Freshly polished steel specimens are used for each run. The surface of the steel is parallel ground to 4 to 8 microinches. The percentages by weight are percentages by weight of the total lubricating oil composition, including the usual additive package. The data are percent decrease in friction according to:

$$\frac{(U_k \text{ of oil alone}) - (U_k \text{ of Additive plus oil})}{(U_k \text{ of oil alone})} \times 100$$

The value for the oil alone would be zero as shown in Table 1 below. Tables 1 and 2 summarize the results.

As can be seen below, the coefficients of friction were reduced up to 59% with the use of these imidazoline-sarcosine reaction products.

TABLE 1

Friction Test Results Using the Low Velocity Friction Apparatus

| Additive | Conc. Wt. % | Percent Reduction In Coefficient of Friction 5 Ft./Min. | 30 Ft./Min. |
|---|---|---|---|
| Test Oil | | | |
| Fully formulated mineral oil containing detergent/dispersant/inhibitor package (10W-40) | — | 0 | 0 |
| Example 1 | | | |
| 2-Heptadecenyl-1-(2-hydroxyethyl) imidazoline/oleoyl sarcosine reaction product | 2 | 59 | 46 |
| Example 2 | | | |
| 2-Heptadecenyl-1-(2-hydroxyethyl) imidazoline/cocoyl sarcosine reaction product | 2 | 36 | 28 |

TABLE 2

Friction Test Results Using Low Velocity Friction Apparatus

| Additive | Conc. Wt. % | Percent Reduction in Coefficient of Friction 5 Ft./Min. | 30 Ft./Min. |
|---|---|---|---|
| Test Oil | | | |
| Fully formulated synthetic automotive engine oil containing detergent/dispersant/inhibitor package - SAE 5W-30 | — | 0 | 0 |
| Example 1 | | | |
| 2-Heptadecenyl-1-(2-hydroxyethyl) imidazoline/oleoyl sarcosine reaction product | 2 | 36 | 30 |

The products of the example were also blended into mineral oil and evaluated for corrosive tendencies. As can be seen from Table 3 below, these imidazoline-sarcosine reaction products were non-corrosive to copper.

TABLE 3

Copper Strip Corrosivity Test Results Using ASTM D-130-80

| | Conc. in 100" Solvent Paraffinic Neutral Lubricating Oil, % | ASTM D130-80 250° F., 3 Hrs | ASTM D130-80 210° F., 6 Hrs |
|---|---|---|---|
| Example 1 | | | |
| 2-Heptadecenyl-1-(2-hydroxyethyl) imidazoline/oleoyl sarcosine reaction product | 1 | 1A* | 1A |
| Example 2 | | | |
| 2-Heptadecenyl-1-(2-hydroxyethyl) imidazoline/oleoyl sarcosine reaction product | 1 | 1A | 1A |

*no corrosion

Hydrocarbyl hydroxyalkyl imidazoline-acyl sarcosine reaction products exhibit good anticorrosion and friction reducing properties and in addition these novel compositions are free from potentially harmful sufur, phosphorus, and metallic components.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A product of reaction obtained by reacting a hydrocarbyl hydroxyalkyl imidazoline and an acyl sarcosine at temperatures of from about 90° to about 250° C. and at atmospheric or higher pressure in a molar ratio of imidazoline to sarcosine of from about 1:1 to about 1:3 wherein said imidazoline has the general formula

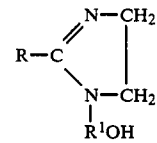

where R is $C_8$–$C_{30}$ hydrocarbyl, and $R^1$ is $C_2$–$C_4$ hydrocarbylene and wherein said sarcosine has the general formula

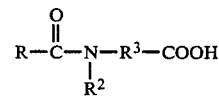

wherein R is as defined above, $R^2$ is $C_1$–$C_6$ hydrocarbyl or hydrogen and $R^3$ is $C_1$–$C_6$ hydrocarbylene.

2. The product of claim 1 wherein said imidazoline is selected from the group consisting of those made by the reaction of a hydroxyalkyl amine with a carboxylic acid selected from the group consisting of oleic, stearic, isostearic, linoleic, tallowyl, lauric, myristic, coco and naphthenic acids.

3. The product of claim 1 wherein said imidazoline is 2-heptadecenyl-1(2-hydroxyethyl)imidazoline.

4. The product of claim 1 wherein said sarcosines are selected from the group consisting of cocoyl, lauroyl, oleoyl, soya and tallowyl sarcosines.

5. The product of claim 4 wherein said sarcosine is oleoyl sarcosine.

6. The product of claim 4 wherein said sarcosine is cocoyl sarcosine.

7. A lubricant composition containing a major proportion of a lubricating oil or a grease prepared therefrom and a minor friction reducing or corrosion inhibiting amount of a product of reaction obtained by reacting a hydrocarbyl hydroxyalkyl imidazoline and an acyl sarcosine in a suitable solvent at temperatures of from about 90° to about 250° C. and at atmospheric or higher pressure in a molar ratio of imidazoline to sarcosine of from about 1:1 to about 1:3 and wherein said imidazoline has the general formula

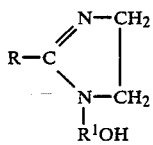

where R is $C_8$–$C_{30}$ hydrocarbyl and $R^1$ is $C_2$–$C_4$ hydrocarbylene, and wherein said sarcosine has the general formula

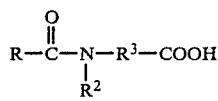

wherein R is as defined above, $R^2$ is $C_1$–$C_6$ hydrocarbyl or hydrogen and $R^3$ is $C_1$–$C_6$ hydrocarbylene.

8. The composition of claim 7 wherein said imidazoline is selected from the group consisting of those made by the reaction of said hydrocarbyl amine with a carboxylic acid selected from the group consisting of oleic, stearic, isostearic, linoleic, tallowyl, lauric, myristic, coco and naphthenic acids.

9. The composition of claim 7 wherein said imidazoline is 2-heptadecenyl-1-(2-hydroxyethyl)imidazoline.

10. The composition of claim 7 wherein said sarcosines are selected from the group consisting of cocoyl, lauroyl, oleoyl, soya and tallowyl sarcosines.

11. The composition of claim 7 wherein said sarcosine is oleoyl sarcosine.

12. The composition of claim 7 wherein said sarcosine is cocoyl sarcosine.

13. The composition of claim 7 wherein said lubricant is a mineral oil.

14. The composition of claim 7 wherein said lubricant is a synthetic oil.

15. The composition of claim 7 wherein said lubricant is a mixture of mineral and synthetic oils.

16. The composition of claim 7 containing from about 0.1 to about 5 wt. % of said product.

17. A method of reducing the friction in an internal combustion engine by treating the moving parts thereof with a lubricating oil or a grease prepared therefrom containing a minor effective amount of a friction reducing and/or corrosion inhibiting product obtained by reacting a hydroxyl-containing alkyl imidazoline and an acyl sarcosine in a suitable solvent at temperatures of from about 90° to about 250° C. and at atmospheric or higher pressure in a molar ratio of imidazoline to sarcosine and from about 1:1 to about 1:3 and wherein said imidazoline has the general formula

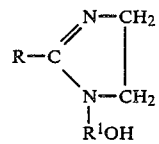

where R is $C_8$–$C_{30}$ hydrocarbyl and $R^1$ is $C_2$–$C_4$ hydrocarbylene, and wherein said sarcosine has the general formula

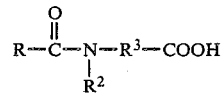

wherein R is as defined above, $R^2$ is $C_1$–$C_6$ hydrocarbyl or hydrogen and $R^3$ is $C_1$–$C_6$ hydrocarbylene.

18. The composition of claim 7 wherein said major proportion is a grease.

* * * * *